(12) United States Patent
Brady et al.

(10) Patent No.: US 8,874,384 B1
(45) Date of Patent: Oct. 28, 2014

(54) METHOD AND DEVICES TO STANDARDIZE ULTRASONIC POROSITY MEASUREMENTS

(75) Inventors: Steven K. Brady, Renton, WA (US);
William P. Motzer, Seattle, WA (US);
Jeffrey R. Kollgaard, Seattle, WA (US);
Nathan R. Smith, Newcastle, WA (US)

(73) Assignee: The Boeing Company, Chicago, IL (US)

(*) Notice: Subject to any disclaimer, the term of this patent is extended or adjusted under 35 U.S.C. 154(b) by 614 days.

(21) Appl. No.: 12/881,679

(22) Filed: Sep. 14, 2010

(51) Int. Cl.
*G01B 17/00* (2006.01)
*G01H 1/08* (2006.01)
*G01N 9/24* (2006.01)

(52) U.S. Cl.
USPC .................................. 702/39; 73/599; 73/600

(58) Field of Classification Search
USPC ....................... 702/39; 73/599, 600
See application file for complete search history.

(56) References Cited

U.S. PATENT DOCUMENTS

| | | | | |
|---|---|---|---|---|
| 3,876,938 A | * | 4/1975 | Ohta et al. | 367/87 |
| 4,856,336 A | * | 8/1989 | Falkevich et al. | 73/598 |
| 5,081,456 A | * | 1/1992 | Michiguchi et al. | 342/22 |
| 5,305,239 A | * | 4/1994 | Kinra | 702/39 |
| 7,353,709 B2 | * | 4/2008 | Kruger et al. | 73/599 |
| 7,617,715 B2 | | 11/2009 | Georgeson et al. | |
| 7,895,895 B2 | * | 3/2011 | Kollgaard et al. | 73/599 |
| 2008/0297309 A1 | * | 12/2008 | Loyer | 340/10.1 |
| 2009/0248141 A1 | * | 10/2009 | Shandas et al. | 623/1.19 |

* cited by examiner

*Primary Examiner* — Michael Nghiem
*Assistant Examiner* — Alexander Statanovsky
(74) *Attorney, Agent, or Firm* — Yee & Associates, P.C.

(57) ABSTRACT

A method of standardizing ultrasonic flaw detectors utilizing electronic porosity standards which includes the steps of obtaining bandwidth characteristics of an ultrasonic flaw detector, obtaining broadband porosity attenuation characteristics of porosity samples, and generating porosity vs. attenuation curves calibrated to the apparatus using the bandwidth characteristics and the broadband porosity attenuation characteristics.

20 Claims, 5 Drawing Sheets

METHOD AND DEVICES TO STANDARDIZE ULTRASONIC POROSITY MEASUREMENTS

TECHNICAL FIELD

The disclosure generally relates to apparatuses and methods for measuring the porosity of materials. More particularly, the disclosure relates to a method and devices to standardize flaw detection using ultrasonic flaw detectors in which electronic porosity standards are used instead of physical porosity standards.

BACKGROUND

Bubbles and other voids trapped within a cured composite laminate comprise the "porosity" of the laminate. An optimally cured composite laminate may have little or no porosity (sometimes described as 0% porosity). The percentage of porosity is defined as the ratio of the part's volume comprised of voids to the volume comprised of solids. In some applications, porosity may weaken a part and render it useless.

In industries such as the aerospace industry in which composite structures are utilized, it may be necessary to determine the porosity of such structures. Accurate measurement of porosity in composite structures may be important in both composite manufacturing and repair. Porosity measurements applied to composite structures may be carried out using ultrasonic attenuation measurements. Ultrasonic attenuation measurement of composite structures is based on the attenuation of ultrasonic energy which occurs by one of two mechanisms when ultrasonic energy impinges against the composite structure. According to the first mechanism, the ultrasonic energy is scattered at interfaces between adjacent structures in a process known as interfacial losses. According to the second mechanism, the ultrasonic energy is attenuated as it propagates through the thickness of the structure in a process known as propagation losses.

The actual ultrasonic attenuation characteristics of a composite structure depends on the properties of the structure, the roughness of its surfaces and the materials at the front and back surfaces of the structure. A system which is commonly known as an ultrasonic testing (UT) flaw detector may be used to measure the ultrasonic attenuation characteristics of a composite structure. A UT flaw detector typically comprises at least a voltage pulser/receiver, signal display capability, signal cable, and ultrasonic transducer. Because each UT flaw detector may have its own effective frequency bandwidth which differs from that of other flaw detectors, two different UT flaw detectors may measure different attenuations on the same composite part, even if both flaw detectors are configured to run at the same frequency (such as 1 MHz). Because propagation attenuation due to porosity is a strong function of ultrasound frequency, different porosity readings for the same composite structure may be obtained using different UT flaw detectors. Therefore, physical porosity standards may be used to standardize the UT flaw detectors for measuring the porosity of composite structures.

One of the drawbacks of using physical porosity standards to standardize UT flaw detectors used in composite structure porosity measurement is that the physical porosity standards are expensive since they are difficult and time-consuming to produce and verify. Moreover, due to the methods by which they are fabricated, physical porosity standards may suffer from some variation in porosity from one batch to another. Shipment of these physical porosity standards around the world to sites where they are used may be necessary. Consequently, the physical porosity standards may not be available when needed. Production of a new set of porosity standards may be an expensive, difficult and time-consuming undertaking.

Therefore, a method and devices to standardize flaw detection using ultrasonic flaw detectors in which electronic porosity standards are used instead of physical porosity standards are needed.

SUMMARY

The disclosure is generally directed to a method of standardizing flaw detection using ultrasonic flaw detectors in which electronic porosity standards are used instead of physical porosity standards. An illustrative embodiment of the method includes obtaining bandwidth characteristics of an ultrasonic flaw detector, obtaining broadband porosity attenuation characteristics of porosity samples and generating porosity vs. attenuation curves calibrated to the apparatus using the bandwidth characteristics and the broadband porosity attenuation characteristics.

The disclosure is further generally directed to a pulse echo flaw detecting ultrasonic system. An illustrative embodiment of the system includes a radio frequency duplexer, a pulse echo ultrasonic flaw detectors interfacing with the radio frequency duplexer, a computer interfacing with the radio frequency duplexer and at least one transducer interfacing with the radio frequency duplexer.

The disclosure is further generally directed to a through-transmission porosity testing ultrasonic system. An illustrative embodiment of the system includes a radio frequency splitter, a through transmission ultrasonic flaw detectors interfacing with the radio frequency splitter, a computer interfacing with the radio frequency splitter and at least one transducer interfacing with the radio frequency splitter.

BRIEF DESCRIPTION OF THE ILLUSTRATIONS

DETAILED DESCRIPTION

Figure 1:
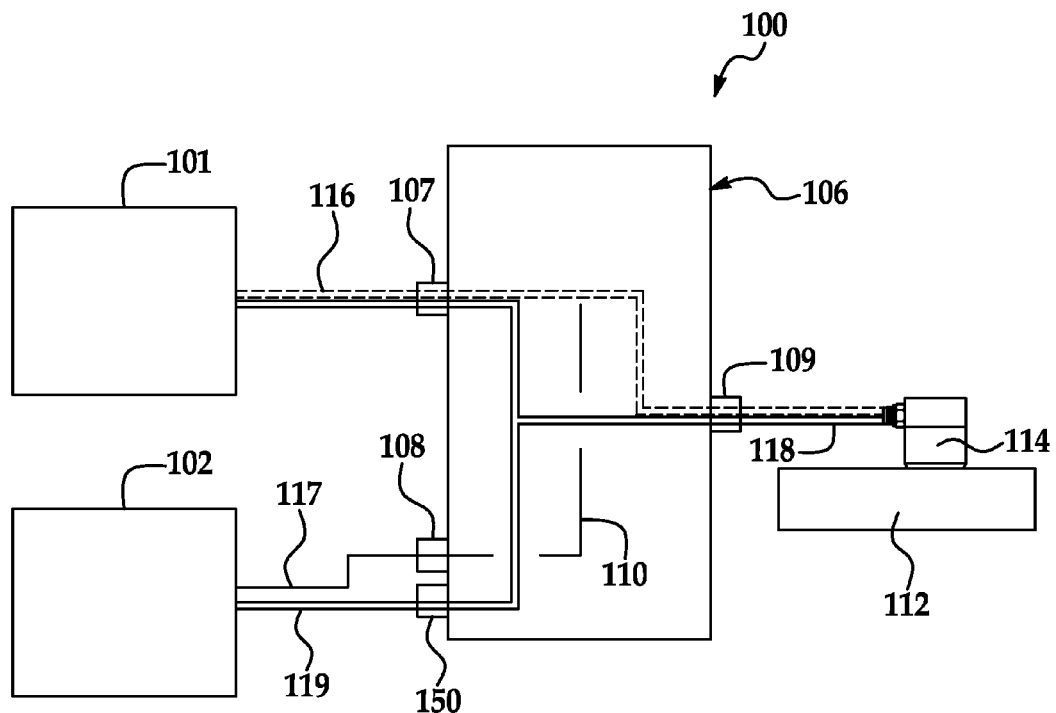
FIG. 1 is a schematic diagram of a pulse echo ultrasonic (PEUT) system.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

The disclosure is generally directed to a method and devices to standardize flaw detecting apparatus in which electronic porosity standards are used instead of physical porosity standards. The method may use porosity standards to determine wideband frequency attenuation characteristics of different levels of porosity. This information may then be used to calculate porosity vs. attenuation curves based on simple local measurements from a specified ultrasound testing apparatus (Pulse Echo Ultrasound (PEUT) or through-transmission ultrasound (TTU)), thereby eliminating the need to use a set of locally available physical porosity standards.

The method may include transmitting ultrasound through a simple reference standard. The simple reference standard may be any material which is inexpensive, homogenous and has well-known attenuation properties. In some embodiments, the simple reference standard may be a block of aluminum or poly (methyl methylacrylate) or PLEXIGLASS (trademark), for example and without limitation. An ultrasonic signal may be transmitted through the reference standard using a flaw detecting apparatus. In some applications, the flaw detecting apparatus may be a conventional pulse echo flaw detecting apparatus (PEUT). In some applications, the flaw detecting apparatus may be a conventional through-transmission ultrasound (TTU) flaw detector. A time-domain, ultrasonic waveform which is specific to the flaw detecting apparatus may be obtained.

The time-domain, ultrasonic waveform may be Fourier transformed into a frequency spectrum. The bandwidth characteristics of the flaw detecting apparatus may be obtained by mathematically removing attenuation effects of the reference standard. Broadband porosity attenuation characteristics of samples having different porosities may be obtained using a flaw detecting apparatus which may be a conventional type flaw detecting apparatus used by ultrasonic inspectors in the field. The broadband porosity attenuation characteristics may be stored as electronic porosity attenuation reference standards. Porosity vs. attenuation curves which are calibrated to some other flaw detecting apparatus may be generated using the bandwidth characteristics of that flaw detecting apparatus and the electronic porosity attenuation reference standards. Actual flaw detecting apparatus of composite structures made using this second flaw detecting apparatus may be compared to the porosity vs. attenuation curves to determine the porosity of the composite structures.

Figure 3:
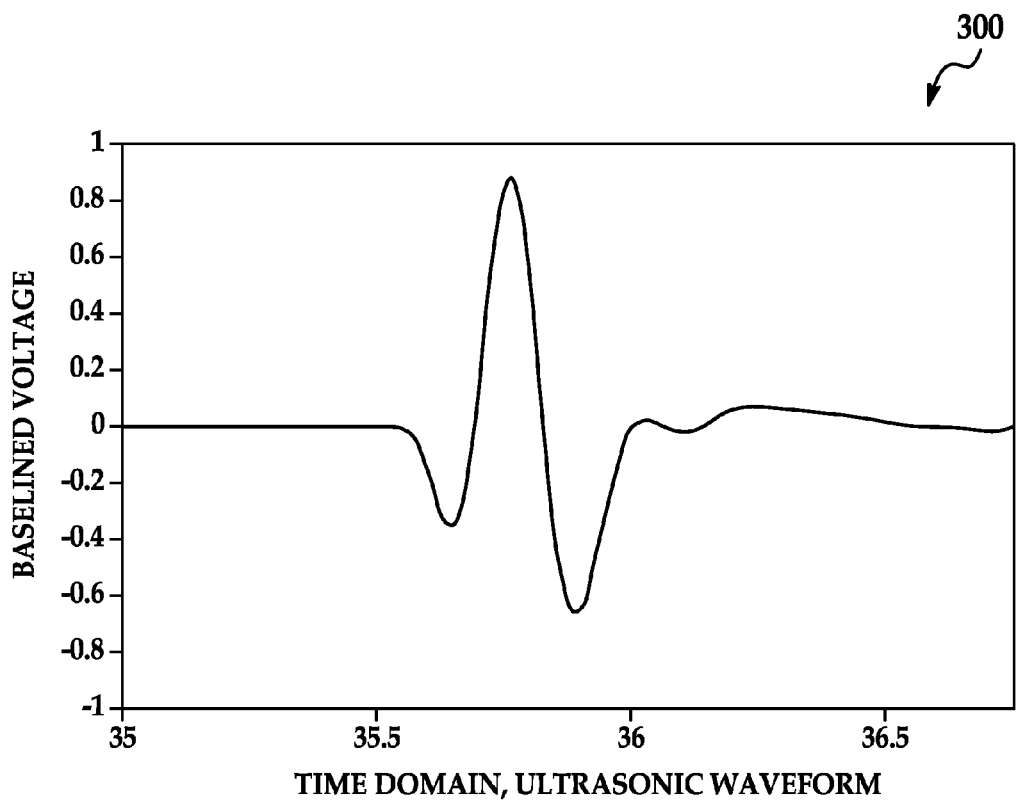
FIG. 3 is a graph which illustrates a time-domain ultrasonic waveform specific to some PEUT or TTU system.
Figure 4:
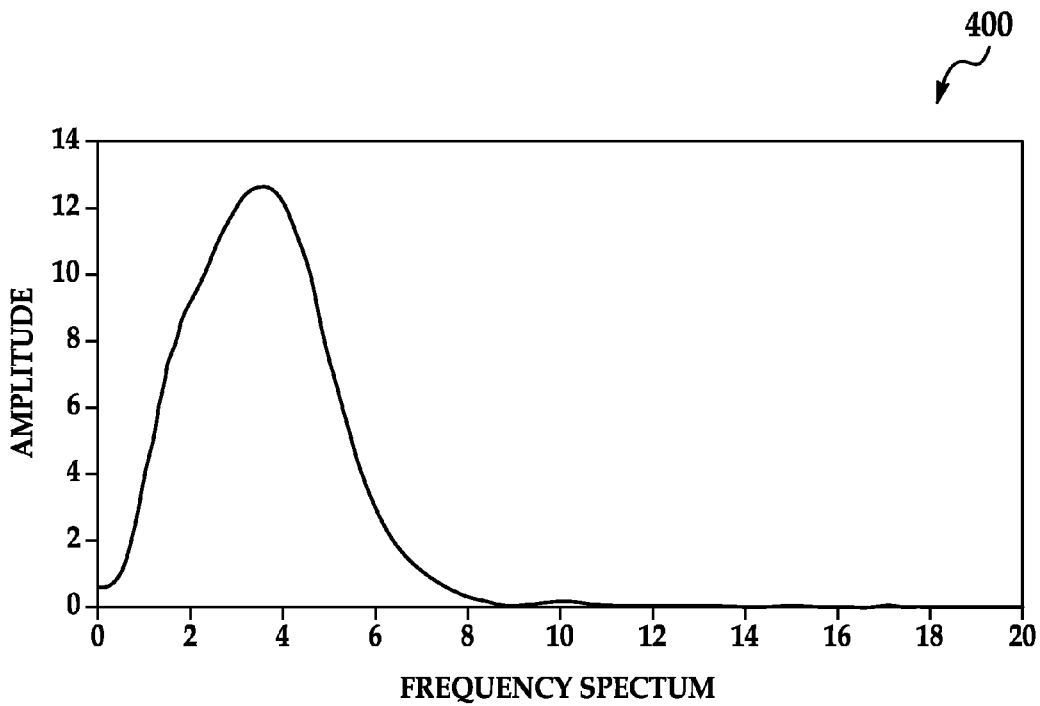
FIG. 4 is a graph which illustrates a frequency spectrum obtained by Fourier transformation of the time-domain ultrasonic waveform in FIG. 3 and indicating bandwidth characteristics of some PEUT or TTU system.

Referring to FIGS. 1, 3 and 4, a pulse echo porosity testing ultrasonic system 100 which is suitable for implementation of the method is shown in FIG. 1. The system 100 may include a pulse echo flaw detecting apparatus (PEUT) 101, hereinafter referred to as "apparatus". A transducer 114 may interface with the apparatus 101 through a signal cable 118. The transducer 114 may emit ultrasonic signals (not shown) through a simple reference standard 112. The apparatus 101, the signal cable 118 and the transducer 114 are commonly known as a "UT flaw detector". The system 100 may be adapted to obtain a time-domain, ultrasonic waveform 300 (FIG. 3) which is specific to the UT flaw detector including the apparatus 101, the signal cable 118 and the transducer 114. The system 100 may be further adapted to save the waveform 300 (FIG. 3) on a PC with A-to-D card 102. In some applications, the waveform 300 (FIG. 3) may be obtained making use of pre-existing outputs (signal and trigger) on the apparatus 101.

As shown in FIG. 1, in some embodiments, the system 100 may include an RF (Radio Frequency) duplexer 106 as an enabler for the disclosed method. The RF duplexer 106 may include an integrated trigger signal generator 110. The apparatus 101 may interface with the RF duplexer 106 through a signal cable 116 and a duplexer port 107. The transducer 114 may interface with the RF duplexer 106 through the inspector's signal cable 118 and a duplexer port 109. The PC with A-to-D card 102 may interface with the RF duplexer 106 through a trigger signal cable 117, a duplexer trigger port 108, a signal cable 119, and a duplexer signal port 150. The transducer 114 may emit and receive ultrasonic signals (not shown) through the reference standard 112. In some embodiments, the transducer 114 may emit ultrasonic signals through the reference standard twice. The RF duplexer 106 may obtain the resulting time-domain, ultrasonic waveform 300 (FIG. 3) from the transducer 114 and transmit the waveform 300 to the PC with A-to-D card 102 and the apparatus 101. The PC with A-to-D card 102 may Fourier transform the time-domain, ultrasonic waveform 300 into a frequency spectrum 400 (FIG. 4) and mathematically remove the attenuation effects of the reference standard 112. The frequency spectrum 400 may be particular to the UT flaw detector including the apparatus 101, the signal cable 118 and the transducer 114 and may be stored on a PC (not shown).

Figure 2:
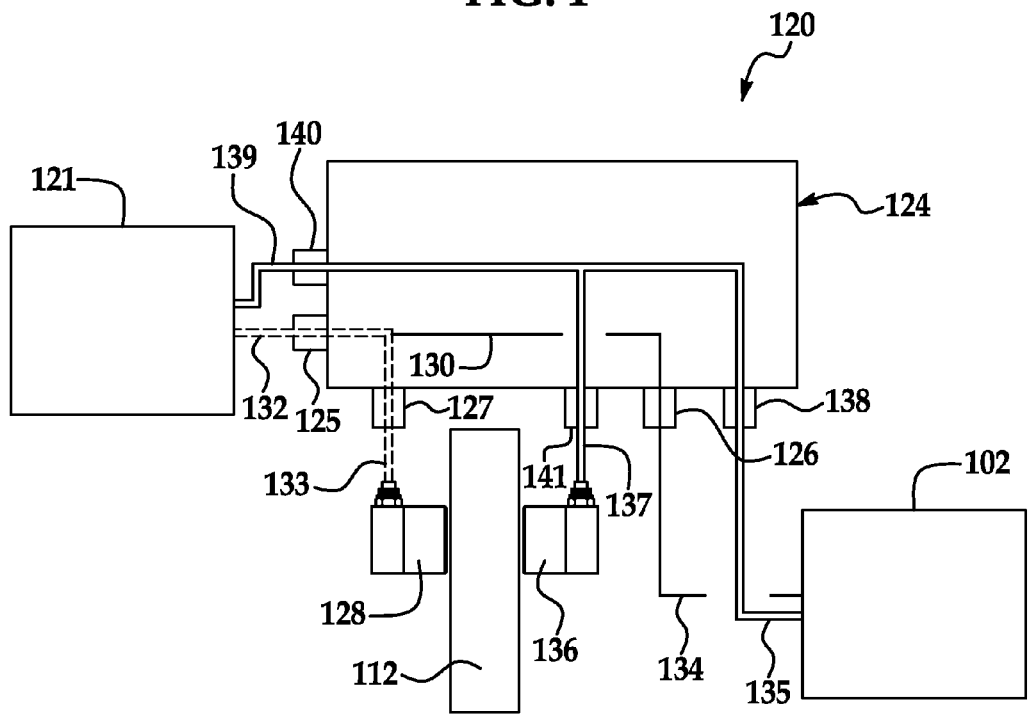
FIG. 2 is a schematic diagram of a through transmission ultrasonic (TTU) system.

Referring to FIG. 2, a through transmission porosity testing ultrasonic system 120 which is suitable for implementation of the method is shown in FIG. 1. The system 120 may include a through transmission flaw detecting apparatus (TTU) 121, hereinafter apparatus. The system 120 may be adapted to obtain a time-domain, ultrasonic waveform 300 (FIG. 3) which is specific to the apparatus 120 and save the waveform on a PC with A-to-D card 102. The ultrasonic transducer 128 emits an ultrasonic signal (not shown) which propagates through the simple reference block 112. The ultrasound is received by ultrasonic transducer 136. The transducers are connected to the splitter 124 with the inspector's signal cables (133 and 137), and ports 127 and 141, respectively. The time-domain ultrasonic waveform 300 which comes through the simple reference block 112 gets to the PC with A-to-D card 102 using signal cable 135, trigger cable 134, and their respective ports 126 and 138 on the splitter 124. The apparatus 121, the inspector cables 133 and 137 and the ultrasonic transducers 128 and 136 are commonly known as a "UT flaw detector".

As further shown in FIG. 2, in some embodiments, the system 120 may include an RF (Radio Frequency) splitter 124 as an enabler for the disclosed method. The RF splitter 124 may include an integrated trigger signal generator 130. The apparatus 121 may interface with the RF splitter 124 through signal cables 132, 139 and splitter ports 125, 140. The transducers 128, 136 may interface with the RF splitter 124 through cables 133, 137 and splitter ports 127, 141. The PC with A-to-D card 102 may interface with the RF splitter 124 through cables 134, 135 and splitter ports 126 and 138. The transducer 128 may emit ultrasonic signals (not shown) into the reference standard 112. The transducer 136 may receive the ultrasonic signal which is emitted by the transducer 128 and passes through the reference standard 112. The RF splitter 124 may obtain the resulting time-domain, ultrasonic waveform from the transducer 136 and transmit the waveform to the PC with A-to-D card 102 and the apparatus 121. The PC with A-to-D card 102 may Fourier transform the time-domain, ultrasonic waveform into a frequency spectrum 400 which may be similar to the frequency spectrum 400 heretofore described with respect to FIG. 4 and mathematically remove the attenuation effects of the reference standard 112. The frequency spectrum may be particular to the UT flaw detector which includes the apparatus 121, the inspector's cables 133 and 137 and the ultrasonic transducers 128 and 136 and may be stored on PC 102.

Figure 5:
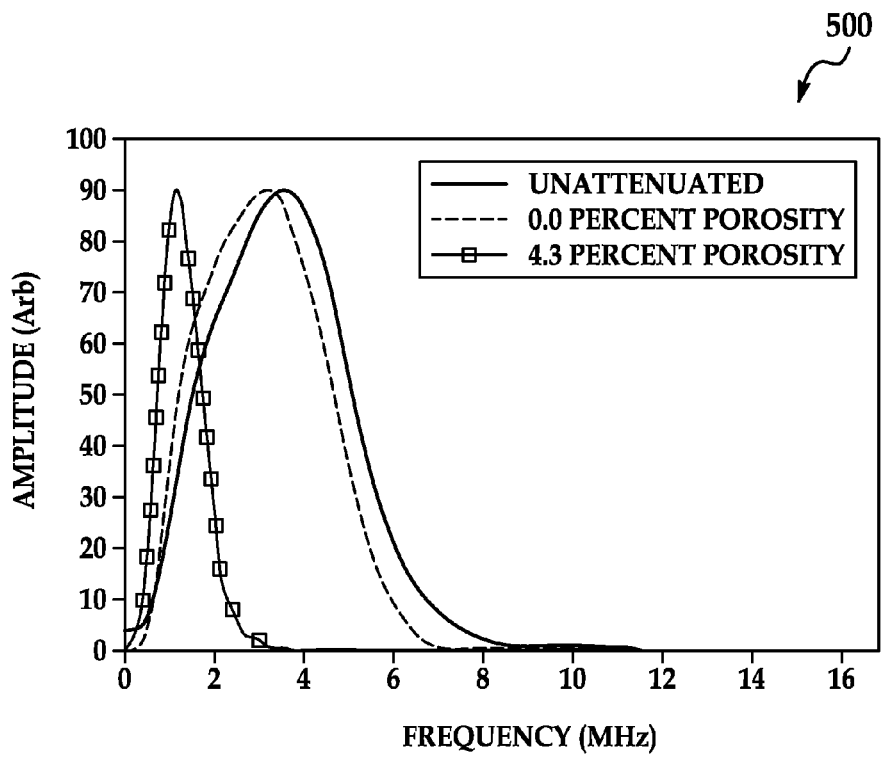
FIG. 5 is a graph which illustrates frequency spectra obtained by transmitting ultrasound through various porosity reference standards.
Figure 6:
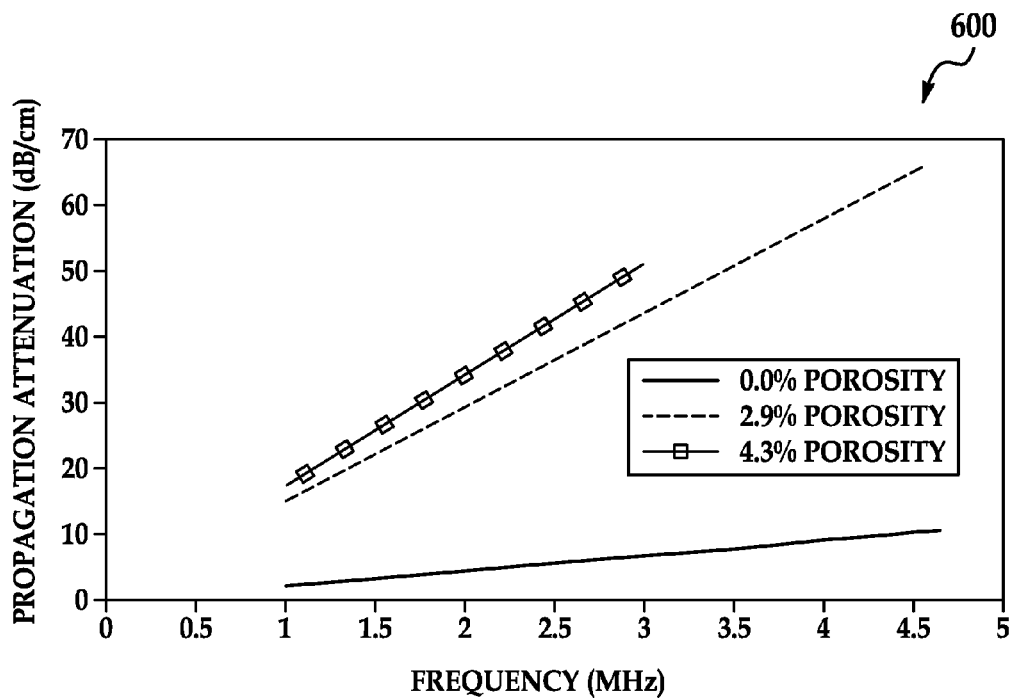
FIG. 6 is a graph which illustrates inherent attenuation characteristics arising from porosity in the various porosity reference standards.

Referring next to FIGS. 5 and 6, the method may further include obtaining broadband porosity attenuation characteristics (FIG. 6) of porosity samples having various porosities. In some applications, the porosity samples may be composite materials having various porosities. A standard or conventional ultrasound (UT) flaw detector (not shown) which is commonly used to measure porosity of materials may be used to transmit ultrasound signals through each of the porosity samples and obtain frequency spectra 500 (FIG. 5) which indicate the broadband porosity attenuation characteristics of the porosity samples. Analysis of the frequency spectra 500 determines the inherent attenuation characteristics 600 (FIG. 6) of the porosity samples. The attenuation characteristics 600 may be electronically stored on PC 102 as electronic porosity attenuation reference standards.

Figure 7:
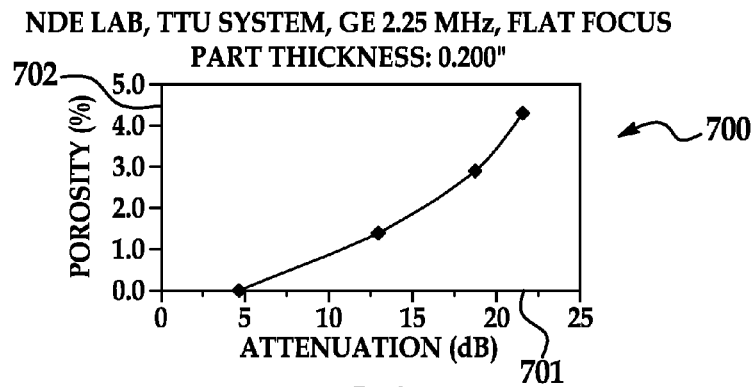
FIG. 7 is a graph which illustrates a calibrated porosity vs. attenuation curve obtained using the bandwidth characteristics of an inspector's UT flaw detector and the inherent attenuation characteristics of the porosity reference standards.

Referring next to FIG. 7, the method may further include generating porosity vs. attenuation curves 700 which are calibrated to any pulse echo ultrasonic (PEUT) flaw detector (pulser/receiver, cable(s), and transducer(s), for example 101, 118, and 114 (FIG. 1)) which is used to measure porosity of a material. The bandwidth characteristics of the frequency spectrum 400 (FIG. 4) which were obtained from the PEUT flaw detector, and the electronic porosity attenuation reference standards 600 (FIG. 6) of the porosity samples may be stored on a PC. Supporting software may enable the PC to generate accurate porosity vs. attenuation curves 700 specific to the PEUT flaw detector in question using the bandwidth characteristics of the frequency spectrum 400 and the electronic porosity attenuation reference standards 600 which describe the inherent attenuation characteristics of porosity samples. The PC may plot the porosity vs. attenuation curves 700 as a graph with attenuation (dB) along the X-axis 701 and porosity (%) along the Y-axis 702. The porosity vs. attenuation curves 700 may be calibrated to the PEUT flaw detector for all thicknesses of the composite structures the porosities of which are to be measured using the PEUT flaw detector. Ultrasonic flaw detection of composite structures in the field may be made using the PEUT flaw detector. The ultrasonic flaw detection results of the composite structures may be compared to the porosity vs. attenuation curves 700 to determine the porosity of the composite structures. With respect to operation of a through-transmission ultrasonic (TTU) flaw detector (pulser/receiver, cable(s), and transducer(s), for example 121, 133, 137, 128 and 136 (FIG. 2)), the same steps may be carried out to obtain the frequency spectra 500 (FIG. 5); the inherent attenuation characteristics 600 (FIG. 6) of the relevant porosity levels in the reference samples stored as electronic porosity attenuation reference standards; and the porosity vs. attenuation curves 700 for various TTU flaw detectors of interest.

Figure 8:
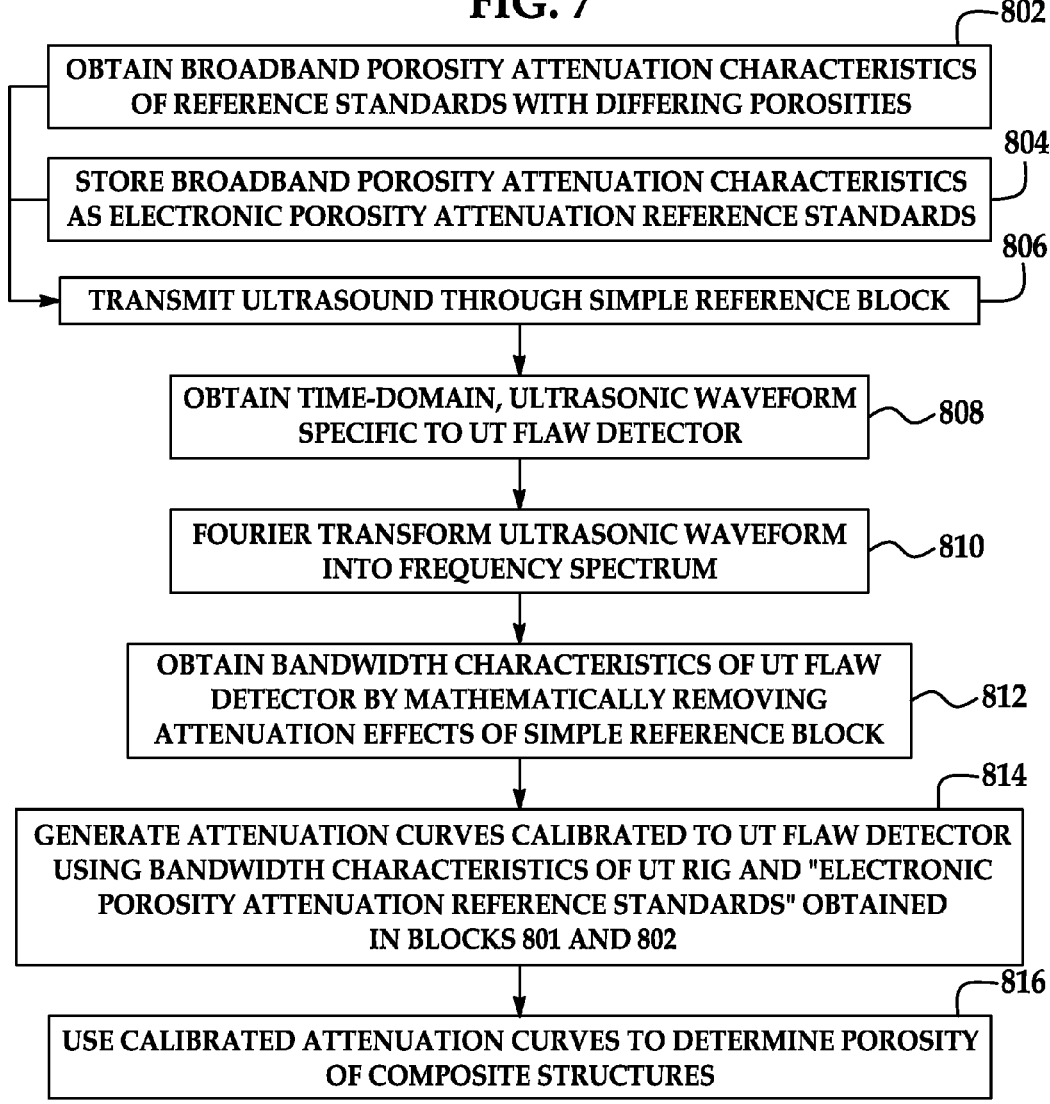
FIG. 8 is a flow diagram of an illustrative embodiment of a method to standardize flaw detection using ultrasonic flaw detectors.

Referring next to FIG. 8, a flow diagram 800 of an illustrative embodiment of a method to standardize ultrasonic flaw detector is shown. In block 802, broadband porosity attenuation characteristics of reference standards with differing porosities are obtained. In block 804, the broadband porosity attenuation characteristics are stored as electronic porosity attenuation reference standards. In block 806, an ultrasonic signal is transmitted through a reference block. In block 808, a time-domain, ultrasonic waveform specific to a UT flaw detector is obtained. In some embodiments, the UT flaw detector may be a pulse echo ultrasonic (PEUT) flaw detector. In some embodiments, the UT flaw detector may be a through-transmission ultrasonic (TTU) UT flaw detector.

In block 810, the ultrasonic waveform which was obtained in block 808 may be Fourier transformed into a frequency spectrum. In block 812, bandwidth characteristics of the apparatus may be obtained by mathematically removing attenuation effects of the reference standard. In block 814, porosity vs. attenuation curves calibrated to the UT flaw detector may be generated using bandwidth characteristics of the apparatus and the electronic attenuation reference standards. In block 816, the porosity vs. attenuation curves may be used to determine the porosity of composite structures.

Figure 9:
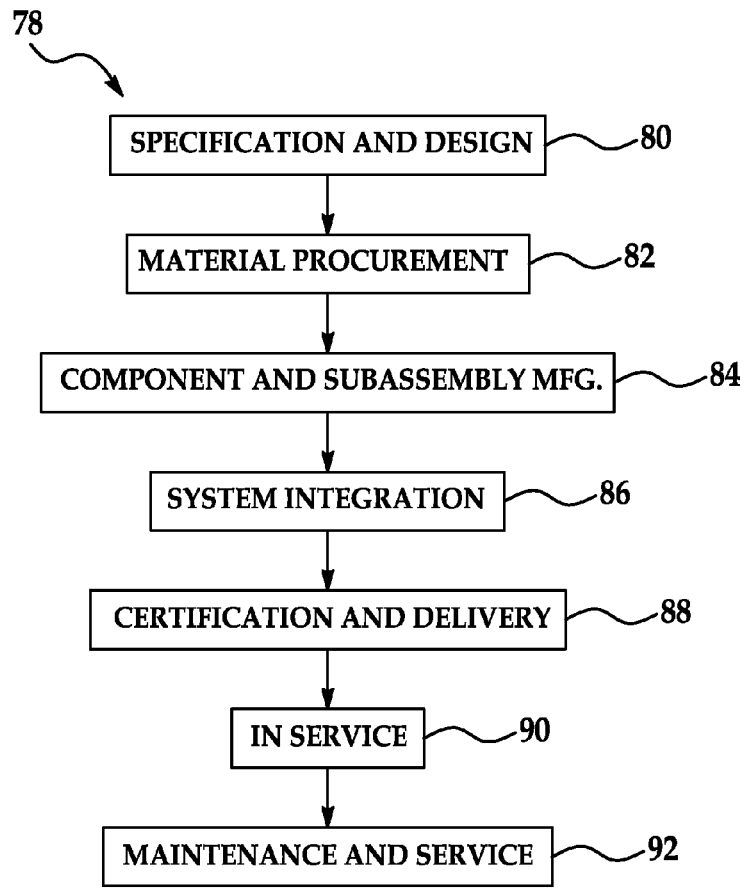
FIG. 9 is a flow diagram of an aircraft production and service methodology.
Figure 10:
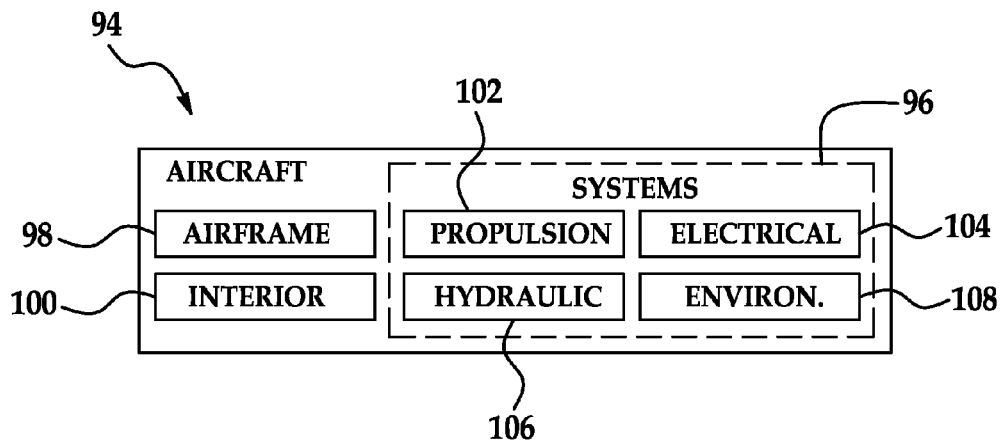
FIG. 10 is a block diagram of an aircraft.

Referring next to FIGS. 9 and 10, embodiments of the disclosure may be used in the context of an aircraft manufacturing and service method 78 as shown in FIG. 9 and an aircraft 94 as shown in FIG. 10. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 10, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method comprising:
   obtaining bandwidth characteristics of an ultrasonic flaw detector, wherein obtaining bandwidth characteristics of the ultrasonic flaw detector comprises transmitting an ultrasonic signal through a reference standard using the ultrasonic flaw detector;
   obtaining broadband porosity attenuation characteristics of porosity samples, the broadband porosity attenuation characteristics of the porosity samples obtained using a second flaw detecting apparatus; and
   generating porosity vs. attenuation curves calibrated to the ultrasonic flaw detector using the bandwidth characteristics of the ultrasonic flaw detector and the broadband porosity attenuation characteristics.

2. The method of claim 1 wherein obtaining bandwidth characteristics of the ultrasonic flaw detector comprises obtaining bandwidth characteristics of a pulse echo flaw detector.

3. The method of claim 1, wherein obtaining bandwidth characteristics of the ultrasonic flaw detector comprises obtaining bandwidth characteristics of a through-transmission ultrasonic flaw detector.

4. The method of claim 1, wherein obtaining bandwidth characteristics of the ultrasonic flaw detector comprises transmitting an ultrasonic signal through the reference standard twice.

5. The method of claim 1, wherein transmitting an ultrasonic signal through the reference standard comprises transmitting an ultrasonic signal through an aluminum reference standard.

6. The method of claim 1, wherein transmitting an ultrasonic signal through the reference standard comprises transmitting an ultrasonic signal through a poly (methyl methylacrylate) reference standard.

7. The method of claim 1, wherein the reference standard comprises a homogenous material having known attenuation properties.

8. The method of claim 7, wherein the reference standard comprises a different material than materials of the porosity samples, wherein the materials of the porosity samples comprise composite materials, and wherein the reference standard comprises one of aluminum or poly (methyl methylacrylate).

9. The method of claim 1, wherein obtaining the bandwidth characteristics of the ultrasonic flaw detector further comprises mathematically removing attenuation effects of the reference standard.

10. The method of claim 1 further comprising:
    obtaining a time-domain, ultrasonic waveform specific to the ultrasonic flaw detector.

11. The method of claim 10, wherein obtaining the time-domain, ultrasonic waveform comprises obtaining the time domain, ultrasonic waveform from a pre-existing output on the ultrasonic flaw detector.

12. The method of claim 10, wherein obtaining the time-domain, ultrasonic waveform comprises interfacing a radio frequency duplexer with the ultrasonic flaw detector, interfacing at least one transducer with the radio frequency duplexer and transmitting an ultrasonic signal from the at least one transducer through the reference standard.

13. The method of claim 12 further comprising interfacing a computer with the radio frequency duplexer and storing the time-domain, ultrasonic waveform on the computer.

14. The method of claim 10, wherein obtaining the time-domain, ultrasonic waveform comprises interfacing a radio frequency splitter with the ultrasonic flaw detector, interfacing at least one transducer with the radio frequency splitter and transmitting an ultrasonic signal from the at least one transducer through the reference standard.

15. The method of claim 14, wherein:
    interfacing the at least one transducer with the radio frequency splitter comprises interfacing a pair of transducers with the radio frequency splitter; and
    transmitting an ultrasonic signal from the at least one transducer through the reference standard comprises transmitting ultrasonic signals from a first one of the pair of transducers through the reference standard to a second one of the pair of transducers.

16. The method of claim 15 further comprising interfacing a computer with the radio frequency splitter and storing the time-domain, ultrasonic waveform on said computer.

17. The method of claim 10 further comprising obtaining a Fourier transformation of the ultrasonic waveform into a frequency spectrum.

18. A pulse echo porosity testing ultrasonic system, comprising:
    a radio frequency duplexer;
    a pulse echo ultrasonic flaw detector interfacing with said radio frequency duplexer;
    a computer interfacing with said radio frequency duplexer, the computer configured to generate porosity vs. attenuation curves calibrated to the ultrasonic flaw detector using bandwidth characteristics of the ultrasonic flaw detector and broadband porosity attenuation characteristics, the broadband porosity attenuation characteristics of the porosity samples obtained using a second flaw detecting apparatus; and
    at least one transducer interfacing with said radio frequency duplexer.

19. The ultrasonic system of claim 18 wherein said radio frequency duplexer comprises a radio frequency duplexer with integrated trigger signal generator.

20. A through-transmission ultrasonic flaw detecting system, comprising:
    a radio frequency splitter;
    a through transmission ultrasonic flaw detector interfacing with said radio frequency splitter;
    a computer interfacing with said radio frequency splitter, the computer configured to generate porosity vs. attenuation curves calibrated to the ultrasonic flaw detector using bandwidth characteristics of the ultrasonic flaw detector and broadband porosity attenuation characteristics, the broadband porosity attenuation characteristics of the porosity samples obtained using a second flaw detecting apparatus; and
    at least one transducer interfacing with said radio frequency splitter.

* * * * *